(12) United States Patent
Vreeland et al.

(10) Patent No.: US 6,828,133 B2
(45) Date of Patent: Dec. 7, 2004

(54) RECOMBINANT VANADIUM HALOPEROXIDASES AND THEIR USES

(75) Inventors: Valerie Vreeland, Berkeley, CA (US); Kwan L. Ng, Oakland, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/840,762

(22) Filed: Apr. 23, 2001

(65) Prior Publication Data

US 2002/0035245 A1 Mar. 21, 2002

Related U.S. Application Data

(63) Continuation of application No. 09/151,189, filed on Sep. 10, 1998, now Pat. No. 6,232,457.

(51) Int. Cl.[7] .............................. C12N 9/08; C12P 21/00
(52) U.S. Cl. ....................................... 435/192; 435/68.1
(58) Field of Search ................................. 435/192, 68.1

(56) References Cited

FOREIGN PATENT DOCUMENTS

WO    WO 95/27046    3/1995

OTHER PUBLICATIONS

Vilter, H., "Vanandium and Its Role in Life", *Biological Systems* 31: 325–362, Marcel Dekker, New York, N.Y., (1995).
Hemrika et al.; *PNAS* (1997) No. 94, pp. 2145–2149.
Itoh et al.; *J. Biological Chemistry* (1986) No. 261, pp. 5194–5200.
Pfeifer, et al.; *J. Gen. Microbiol* (1992) No. 138, pp. 1123–1131.
Rush, et al.; *FEBS Letters* (1995) 359:244–246.
Sheffield et al.; *Phytochemistry* (1993) No. 32, pp. 21–26.
Shimonshi et al.; "Cloning and Expression of the Gene for a Vanadium–dependent Bromoperoxidase from a Marine Macro–alga, *Corallina pilulifera*" *FEBS Lett.* (1998) No. 428, pp. 105–110.
Simons et al.; *European Journal of Biochem* (1995) No. 229, pp. 566–574.
Soedjak, et al. "Inhibition and Inactivation of Vanadium Bromoperoxidase by the Substrate Hydrogen Peroxide and Further Mechanistic Studies" *Biochemistry* (Oct. 1995) vol. 34(39), pp. 12689–12696.
Soedjak, et al. "Mechanism of Dioxygen Formation Catalyzed by Vanadium Bromoperoxidase From *Macrocystis pyrifera* and *Fucus distichus*: Steady State Kinetic Analysis and Comparison to the Mechanism of V–BrPO from *Ascophyllum nodosum*" *Biochim Biophys Acta.* (Aug. 1991) vol. 1079(1), pp. 1–7.
Soedjak, et al. "Characterization of Vanadium Bromoperoxidase from Macrocystis and Fucus: Reactivity of Vanadium Bromoperoxidase Toward Acyl and Alkyl Peroxides and Bromination of Amines" *Biochemistry* (Aug. 1990) vol. 29(34), pp. 7974–7981.
Van Pee, K.H.; *J. Bacterioll* (1988) No. 170, pp. 5890–5894.
Vreeland et al.; *Molecular Biology of the Cell 7 (Supplement)* 304a (1996).
Whitwam, R.E.; "Biophys. Research Communications." *Biochem* (1995) No. 216, pp. 1013–1017.

*Primary Examiner*—Charles L. Patterson, Jr.
(74) *Attorney, Agent, or Firm*—Townsend and Townsend and Crew LLP

(57) ABSTRACT

The present invention provides new recombinantly produced vanadium bromoperoxidases. The enzymes are useful in a number of industrial applications.

12 Claims, 1 Drawing Sheet

```
                              SEQUENCE LISTING

<160> NUMBER OF SEQ ID NOS: 11

<210> SEQ ID NO 1
<211> LENGTH: 2931
<212> TYPE: DNA
<213> ORGANISM: Fucus distichus
<220> FEATURE:
<221> NAME/KEY: CDS
<222> LOCATION: (228)..(2258)
<223> OTHER INFORMATION: vanadium bromoperoxidase

<400> SEQUENCE: 1
cgcggacaag ccttggaaga gaggttgccc aattcaacag agcgaggccc gtgaaggtgt      60
ggaggacacg tgctacaagc tgatccacga gagcctcaac ttccctactg atacgggagt     120
ttgtactgcg ccgcgttgcc aaaaaccgca actttaaaca gcgctcgcga gcgccacatg     180
cttcccacgc atccacaaaa tcgacagtgg tatcgctgag cttgaat atg ctt tgc       236
                                                    Met Leu Cys
                                                      1 cat gca gcg gac acg aca aga ggc tct cct atg cct gac acc gga gtg       284
His Ala Ala Asp Thr Thr Arg Gly Ser Pro Met Pro Asp Thr Gly Val
      5                  10                  15 ctt cgg ttg ctc aca tca gag cag cgc gct aaa ggt tgg aga cgc cag       332
Leu Arg Leu Leu Thr Ser Glu Gln Arg Ala Lys Gly Trp Arg Arg Gln
 20                  25                  30                  35 tta gag ggg gag aaa tca cta ggt ttt cat cca agc gag acg cct tat       380
Leu Glu Gly Glu Lys Ser Leu Gly Phe His Pro Ser Glu Thr Pro Tyr
                 40                  45                  50 atc aag tac ttg gaa ggc tct gag act tgg aag aag gtt aag ctt cca       428
Ile Lys Tyr Leu Glu Gly Ser Glu Thr Trp Lys Lys Val Lys Leu Pro
             55                  60                  65 acg gac ggc ata tcg gct tcc aag atc ctg ggt aaa att atg gcc agg       476
Thr Asp Gly Ile Ser Ala Ser Lys Ile Leu Gly Lys Ile Met Ala Arg
         70                  75                  80 gtc cgc atc gct acc gcc ttg gct gtg gta ctg gcc gca ccc tgt ttg       524
Val Arg Ile Ala Thr Ala Leu Ala Val Val Leu Ala Ala Pro Cys Leu
     85                  90                  95 gca ttc gac gag gtc aca gcc agt ggt gtt ttc cct gag gaa cac aag       572
Ala Phe Asp Glu Val Thr Ala Ser Gly Val Phe Pro Glu Glu His Lys
100                 105                 110                 115 cac acc ggg gag gga aga cac ctc cag acc tgt aca aac tcc gac gat       620
His Thr Gly Glu Gly Arg His Leu Gln Thr Cys Thr Asn Ser Asp Asp
                120                 125                 130 gcg ctg gat ccg acg gcg ccg aat aga agg gac aac gta gct ttt gcg       668
Ala Leu Asp Pro Thr Ala Pro Asn Arg Arg Asp Asn Val Ala Phe Ala
            135                 140                 145 tcg cgg cgc gat gcc gcc agg cga gaa cgt gac ggg aca ggg act gtc       716
Ser Arg Arg Asp Ala Ala Arg Arg Glu Arg Asp Gly Thr Gly Thr Val
        150                 155                 160 tgc caa atc act aac gga gaa act gat ttg gct acc atg ttc cac aag       764
Cys Gln Ile Thr Asn Gly Glu Thr Asp Leu Ala Thr Met Phe His Lys
    165                 170                 175
```

```
tct ctg cca cac gat gaa ctg gga cag gta acc gca gac gac ttc gct      812
Ser Leu Pro His Asp Glu Leu Gly Gln Val Thr Ala Asp Asp Phe Ala
180                 185                 190                 195 atc ctc gag gac tgc atc tta aac gga gat ttc agc att tgc gag gac      860
Ile Leu Glu Asp Cys Ile Leu Asn Gly Asp Phe Ser Ile Cys Glu Asp
                200                 205                 210 gtg cct gcg gga gac ccg gcg ggt cgc ctc gtc aat cct acc gct gcg      908
Val Pro Ala Gly Asp Pro Ala Gly Arg Leu Val Asn Pro Thr Ala Ala
            215                 220                 225 ttt gcc atc gac ata tcc ggt ccc gca ttc tcg gct acg aca ata ccc      956
Phe Ala Ile Asp Ile Ser Gly Pro Ala Phe Ser Ala Thr Thr Ile Pro
        230                 235                 240 ccg gta cct acc ctt tcc tct cct gag ctc gcc gct cag ttg gcg gag     1004
Pro Val Pro Thr Leu Ser Ser Pro Glu Leu Ala Ala Gln Leu Ala Glu
    245                 250                 255 cta tac tgg atg gcg ctg gcc agg gat gta ccc ttt atg cag tat ggc     1052
Leu Tyr Trp Met Ala Leu Ala Arg Asp Val Pro Phe Met Gln Tyr Gly
260                 265                 270                 275 acc gac gaa att acc act acc gcg gca gcc aac ctc gct gga atg gga     1100
Thr Asp Glu Ile Thr Thr Thr Ala Ala Ala Asn Leu Ala Gly Met Gly
                280                 285                 290 ggc ttc cca aat ctg gac gcc gtg tcg ata ggg tcc gat ggt acg gtg     1148
Gly Phe Pro Asn Leu Asp Ala Val Ser Ile Gly Ser Asp Gly Thr Val
            295                 300                 305 gac ccg ttc tcc cag ctc ttc cga gcg acc ttc gtt ggt gtt gaa acg     1196
Asp Pro Phe Ser Gln Leu Phe Arg Ala Thr Phe Val Gly Val Glu Thr
        310                 315                 320 ggg ccc ttt gtc tct cag ctg ctc gtg aac agc ttc acc atc gac gct     1244
Gly Pro Phe Val Ser Gln Leu Leu Val Asn Ser Phe Thr Ile Asp Ala
    325                 330                 335 att acg gtc gaa ccg aag cag gag aca ttc gcc ccc gac ttg aac tat     1292
Ile Thr Val Glu Pro Lys Gln Glu Thr Phe Ala Pro Asp Leu Asn Tyr
340                 345                 350                 355 atg gtc gat ttt gac gaa tgg ctg aac att cag aat ggt gga ccc ccg     1340
Met Val Asp Phe Asp Glu Trp Leu Asn Ile Gln Asn Gly Gly Pro Pro
                360                 365                 370 gcc ggc ccc gaa gag tta gac gaa gag ctg cgt ttt atc cgt aac gcc     1388
Ala Gly Pro Glu Glu Leu Asp Glu Glu Leu Arg Phe Ile Arg Asn Ala
            375                 380                 385 cgc gac ctg gcc agg gtc tcc ttc gtg gac aat atc aac acc gaa gct     1436
Arg Asp Leu Ala Arg Val Ser Phe Val Asp Asn Ile Asn Thr Glu Ala
        390                 395                 400 tat cgc ggg tct ctt atc cta ctt gag ctg gga gcc ttc agc agg ccc     1484
Tyr Arg Gly Ser Leu Ile Leu Leu Glu Leu Gly Ala Phe Ser Arg Pro
    405                 410                 415 ggt atc aac ggt cca ttc atc gac agt gat cgg cag gcg ggc ttc gtc     1532
Gly Ile Asn Gly Pro Phe Ile Asp Ser Asp Arg Gln Ala Gly Phe Val
420                 425                 430                 435 aac ttc ggc acg tct cac tac ttc aga ttg ata ggt gcc gcc gag ctg     1580
Asn Phe Gly Thr Ser His Tyr Phe Arg Leu Ile Gly Ala Ala Glu Leu
                440                 445                 450 gcg cag cgt gcc tcg tgt tac caa aag tgg cag gtg cat cga ttt gca     1628
Ala Gln Arg Ala Ser Cys Tyr Gln Lys Trp Gln Val His Arg Phe Ala
            455                 460                 465 cgc ccc gag gct ctc ggg ggt acc ctc cac aac acc atc gcg ggg gat     1676
Arg Pro Glu Ala Leu Gly Gly Thr Leu His Asn Thr Ile Ala Gly Asp
        470                 475                 480
```

```
cta gat gca gac ttc gac atc tcc ctt ctt gaa aat gat gag ctc ttg    1724
Leu Asp Ala Asp Phe Asp Ile Ser Leu Leu Glu Asn Asp Glu Leu Leu
    485                 490                 495 aaa cgt gtg gcg gag ata aat gcg gcg cag aat ccc aac aac gag gtc    1772
Lys Arg Val Ala Glu Ile Asn Ala Ala Gln Asn Pro Asn Asn Glu Val
500                 505                 510                 515 acc tac ctt ctt cca caa gct atc caa gtg gga tcg cca acg cac cct    1820
Thr Tyr Leu Leu Pro Gln Ala Ile Gln Val Gly Ser Pro Thr His Pro
                520                 525                 530 tcc tac ccg tcc ggc cac gct acc caa aat gga gca ttt gcc aca gtt    1868
Ser Tyr Pro Ser Gly His Ala Thr Gln Asn Gly Ala Phe Ala Thr Val
            535                 540                 545 ctg aag gcc ctc att ggc cta gat cgg gga ggt gag tgc ttc cct aac    1916
Leu Lys Ala Leu Ile Gly Leu Asp Arg Gly Gly Glu Cys Phe Pro Asn
        550                 555                 560 ccc gtg ttc cca agc gat gac ggc ctg gaa cta atc aac ttc gaa ggg    1964
Pro Val Phe Pro Ser Asp Asp Gly Leu Glu Leu Ile Asn Phe Glu Gly
    565                 570                 575 gca tgc ctt aca tat gag gga gag atc aac aag ctc gcg gtc aac gtc    2012
Ala Cys Leu Thr Tyr Glu Gly Glu Ile Asn Lys Leu Ala Val Asn Val
580                 585                 590                 595 gca ttt ggg agg cag atg ctg ggc atc cac tat cgg ttc gac ggt atc    2060
Ala Phe Gly Arg Gln Met Leu Gly Ile His Tyr Arg Phe Asp Gly Ile
                600                 605                 610 caa ggc cta ctt ctc gga gag aca atc act gta cga aca ctt cac cag    2108
Gln Gly Leu Leu Leu Gly Glu Thr Ile Thr Val Arg Thr Leu His Gln
            615                 620                 625 gag ctg atg acg ttc gcc gag gaa gcc acc ttt gaa ttc cgc tta ttc    2156
Glu Leu Met Thr Phe Ala Glu Glu Ala Thr Phe Glu Phe Arg Leu Phe
        630                 635                 640 acc gga gag gtc atc aaa ctt ttc cag gac ggg aca ttc tcc atc gat    2204
Thr Gly Glu Val Ile Lys Leu Phe Gln Asp Gly Thr Phe Ser Ile Asp
    645                 650                 655 gga gat atg tgt tcc ggt ttg gtt tac act ggc gtg gcg gac tgc cag    2252
Gly Asp Met Cys Ser Gly Leu Val Tyr Thr Gly Val Ala Asp Cys Gln
660                 665                 670                 675 gct tagtgcagaa aataataatt gtcggatgct aaaatgcac ccacgaccaa          2305
Ala gtcgtcgagt cacgtcgccg gagcatcctt cagcgaaaaa ggagagtaac ctatatgcta  2365
tagaggagaa ccacggagta caatgcaggt tcttttacca tgtacattgg attgcagtaa  2425
gtgcggttag agagggatac gttaaacgtg cttgcctgtg tatatgatac atttgtcatg  2485
gaaatattag aatgcgttga cttgacttca ccatgaaata ccatgatcgc gtggtgtgct  2545
gctttcacct gtcggagcgg tacgtaagat gtgctttcta ctgagccgtt tgtgtttagt  2605
ccattccgcg tggcagtgta aacaaagagg atgtagtctc gccctcagtt tggagagtac  2665
cgtaggtggc aggacgtata tctctggtag cggtctgtta agaacttcca caagaccgtt  2725
tacgtttggt tgtttagtcg atgcctcttc gttacttgac cgatccattg agagtacctg  2785
taccagtatg gtgtaagaca tattttctc ctgttatgga tctgtagaac agctaggtgt   2845
tgttttatac acaggatgct ataaaatagg gatgttgata atggcatcgg tactcatgaa  2905
accgcaaaat ggcgatagat attccc                                       2931

<210> SEQ ID NO 2
<211> LENGTH: 676
<212> TYPE: PRT
<213> ORGANISM: Fucus distichus
```

```
<400> SEQUENCE: 2

Met Leu Cys His Ala Ala Asp Thr Thr Arg Gly Ser Pro Met Pro Asp
  1               5                  10                  15

Thr Gly Val Leu Arg Leu Leu Thr Ser Glu Gln Arg Ala Lys Gly Trp
             20                  25                  30

Arg Arg Gln Leu Glu Gly Glu Lys Ser Leu Gly Phe His Pro Ser Glu
         35                  40                  45

Thr Pro Tyr Ile Lys Tyr Leu Glu Gly Ser Glu Thr Trp Lys Lys Val
     50                  55                  60

Lys Leu Pro Thr Asp Gly Ile Ser Ala Ser Lys Ile Leu Gly Lys Ile
 65                  70                  75                  80

Met Ala Arg Val Arg Ile Ala Thr Ala Leu Ala Val Leu Ala Ala
                 85                  90                  95

Pro Cys Leu Ala Phe Asp Glu Val Thr Ala Ser Gly Val Phe Pro Glu
                100                 105                 110

Glu His Lys His Thr Gly Glu Gly Arg His Leu Gln Thr Cys Thr Asn
            115                 120                 125

Ser Asp Asp Ala Leu Asp Pro Thr Ala Pro Asn Arg Arg Asp Asn Val
    130                 135                 140

Ala Phe Ala Ser Arg Arg Asp Ala Ala Arg Glu Arg Asp Gly Thr
145                 150                 155                 160

Gly Thr Val Cys Gln Ile Thr Asn Gly Glu Thr Asp Leu Ala Thr Met
                165                 170                 175

Phe His Lys Ser Leu Pro His Asp Glu Leu Gly Gln Val Thr Ala Asp
                180                 185                 190

Asp Phe Ala Ile Leu Glu Asp Cys Ile Leu Asn Gly Asp Phe Ser Ile
            195                 200                 205

Cys Glu Asp Val Pro Ala Gly Asp Pro Ala Gly Arg Leu Val Asn Pro
210                 215                 220

Thr Ala Ala Phe Ala Ile Asp Ile Ser Gly Pro Ala Phe Ser Ala Thr
225                 230                 235                 240

Thr Ile Pro Pro Val Pro Thr Leu Ser Ser Pro Glu Leu Ala Ala Gln
                245                 250                 255

Leu Ala Glu Leu Tyr Trp Met Ala Leu Ala Arg Asp Val Pro Phe Met
                260                 265                 270

Gln Tyr Gly Thr Asp Glu Ile Thr Thr Thr Ala Ala Asn Leu Ala
            275                 280                 285

Gly Met Gly Gly Phe Pro Asn Leu Asp Ala Val Ser Ile Gly Ser Asp
    290                 295                 300

Gly Thr Val Asp Pro Phe Ser Gln Leu Phe Arg Ala Thr Phe Val Gly
305                 310                 315                 320

Val Glu Thr Gly Pro Phe Val Ser Gln Leu Leu Val Asn Ser Phe Thr
                325                 330                 335

Ile Asp Ala Ile Thr Val Glu Pro Lys Gln Glu Thr Phe Ala Pro Asp
            340                 345                 350

Leu Asn Tyr Met Val Asp Phe Asp Glu Trp Leu Asn Ile Gln Asn Gly
        355                 360                 365

Gly Pro Pro Ala Gly Pro Glu Glu Leu Asp Glu Glu Leu Arg Phe Ile
    370                 375                 380

Arg Asn Ala Arg Asp Leu Ala Arg Val Ser Phe Val Asp Asn Ile Asn
385                 390                 395                 400
```

Thr Glu Ala Tyr Arg Gly Ser Leu Ile Leu Leu Glu Leu Gly Ala Phe
            405                 410                 415

Ser Arg Pro Gly Ile Asn Gly Pro Phe Ile Asp Ser Asp Arg Gln Ala
            420                 425                 430

Gly Phe Val Asn Phe Gly Thr Ser His Tyr Phe Arg Leu Ile Gly Ala
            435                 440                 445

Ala Glu Leu Ala Gln Arg Ala Ser Cys Tyr Gln Lys Trp Gln Val His
    450                 455                 460

Arg Phe Ala Arg Pro Glu Ala Leu Gly Gly Thr Leu His Asn Thr Ile
465                 470                 475                 480

Ala Gly Asp Leu Asp Ala Asp Phe Asp Ile Ser Leu Leu Glu Asn Asp
            485                 490                 495

Glu Leu Leu Lys Arg Val Ala Glu Ile Asn Ala Ala Gln Asn Pro Asn
            500                 505                 510

Asn Glu Val Thr Tyr Leu Leu Pro Gln Ala Ile Gln Val Gly Ser Pro
            515                 520                 525

Thr His Pro Ser Tyr Pro Ser Gly His Ala Thr Gln Asn Gly Ala Phe
            530                 535                 540

Ala Thr Val Leu Lys Ala Leu Ile Gly Leu Asp Arg Gly Gly Glu Cys
545                 550                 555                 560

Phe Pro Asn Pro Val Phe Pro Ser Asp Asp Gly Leu Glu Leu Ile Asn
            565                 570                 575

Phe Glu Gly Ala Cys Leu Thr Tyr Glu Gly Glu Ile Asn Lys Leu Ala
            580                 585                 590

Val Asn Val Ala Phe Gly Arg Gln Met Leu Gly Ile His Tyr Arg Phe
            595                 600                 605

Asp Gly Ile Gln Gly Leu Leu Leu Gly Glu Thr Ile Thr Val Arg Thr
            610                 615                 620

Leu His Gln Glu Leu Met Thr Phe Ala Glu Glu Ala Thr Phe Glu Phe
625                 630                 635                 640

Arg Leu Phe Thr Gly Glu Val Ile Lys Leu Phe Gln Asp Gly Thr Phe
            645                 650                 655

Ser Ile Asp Gly Asp Met Cys Ser Gly Leu Val Tyr Thr Gly Val Ala
            660                 665                 670

Asp Cys Gln Ala
        675

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence:probe for
    second conserved region between Curvularia and
    Ascophyllum vanadium peroxidase active sites

<400> SEQUENCE: 3
ccaacgcacc cttcgtaccc gtctggccac gctacccaaa acggagcatt t                    51

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence:probe for
    third conserved region between Curvularia and
    Ascophyllum vanadium peroxidase active sites

```
<400> SEQUENCE: 4
ccgtacgaac acttcaccag gagctgatga ctttcgccga ggaatccacc t        51

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence:Fucus
      peroxidase ligation independent cloning (LIC) 5'
      primer for full length construct

<400> SEQUENCE: 5
gacgacgaca atatgctttg ccatgcagcg gaca                            34

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence:Fucus
      peroxidase ligation independent cloning (LIC) 5'
      primer for mid length construct

<400> SEQUENCE: 6
gacgacgaca agatggcgcc gaatagaagg gacaa                           35

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence:Fucus
      peroxidase ligation independent cloning (LIC) 5'
      primer for short construct

<400> SEQUENCE: 7
gacgacgaca agatgctctt ccgagcgacc ttc                             33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence:Fucus
      peroxidase ligation independent cloning (LIC) 3'
      primer for full length, mid length and short
      constructs

<400> SEQUENCE: 8
gaggagaagc ccggttgcac taagcctggc agt                             33

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence:conserved
      vanadium-binding region 1, amino acids 452-473

<400> SEQUENCE: 9

Ala Gln Arg Ala Ser Cys Tyr Gln Lys Trp Gln Val His Arg Phe Ala
 1               5                  10                  15

Arg Pro Glu Ala Leu Gly
            20
```

```
<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence:conserved
      vanadium-binding region 2, amino acids 528-546

<400> SEQUENCE: 10

Pro Thr His Pro Ser Tyr Pro Ser Gly His Ala Thr Gln Asn Gly Ala
 1               5                  10                  15

Phe Ala Thr

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence:conserved
      vanadium-binding region 3, amino acids 591-609

<400> SEQUENCE: 11

Leu Ala Val Asn Val Ala Phe Gly Arg Gln Met Leu Gly Ile His Tyr
 1               5                  10                  15

Arg Phe Asp
```

RECOMBINANT VANADIUM HALOPEROXIDASES AND THEIR USES

This application is a continuation of U.S. patent application Ser. No. 09/151,189 filed Sep. 10, 1998, now U.S. Pat. No. 6,232,457 which is incorporated herein by reference.

FIELD OF THE INVENTION

The present invention relates to cloning and recombinant expression of proteins. In particular, it relates to expression of vanadium bromoperoxidase polypeptides.

BACKGROUND OF THE INVENTION

Vanadium haloperoxidase enzymes are useful in industrial catalysis in a variety of contexts (Sheffield, et al., *Biotechnology Techniques*, 8:579–582 (1994)). For instance, they catalyze a variety of halogenation, oxidation and epoxidation reactions (Itoh, et al., *Eur. J. Biochem.*, 172:477 (1988); Itoh, et. al. *Biochimica et Biophysica Acta.*, 1994 (1993); Itoh, et al., *Appl. Microbiol. & Biotechnol.*, 43:394–401 (1995)). Although a halide ion is a required cofactor for enzyme activity, products may not be halogenated. Numerous uses in synthetic organic chemistry include reactions with diverse substrates such as aliphatic and aromatic hydrocarbons, phenols, β-diketones and nitrogen- and sulfur-containing heterocycles (Itoh, et al., *Eur. J. Biochem.* 172:477 (1988); Neidleman et al., *Biohalogenation: Principles, Basic Roles and Applications*, Ellis Horwood, John Wiley & Sons, New York (1986)). Bromoperoxidases can also be used in place of synthetic organic chemistry reactions to make activated intermediates or products such as pesticides. In addition, these enzymes have an advantage over chemical synthesis in producing stereospecific products (Itoh, et al., *Eur. J. Biochem.*, 172:477 (1988)). Moreover, haloperoxidases have unusual stability (both temporal and thermal) and are active in solvents including methanol, ethanol and acetone.

Recent medical applications of bromoperoxidase have been described. Lovqvist, et al., *Nuclear Medicine and Biology*, 22:125–131 (1995) described the enzymatic bromination of a monoclonal antibody with BR-radionuclide for imaging of antibody localization by PET scanning. There is current interest in enzymatic production of antibiotics including fosfomycin and pyrrolnitrin (Itoh, et. al. *Biochimica et Biophysica Acta*. 1994 (1993); Itoh, et al., *Appl. Microbiol. & Biotechnol*. 43:394–401 (1995)) and 7-chlorotetracycline (van Pée, K. H., *J. Bacteriol.*, 170:5890–5894 (1988)) via haloperoxidase-catalyzed reactions in bacteria.

Known haloperoxidases include bromoperoxidases from brown and red algae including *Fucus* and *Ascophyllum* (Butler, et al., *Chem. Rev.*, 93:1937–1994 (1993)), iodoperoxidase from green algae (Mehrtens, G., *Polar Biol.* 14:351–354 (1994)), and chloroperoxidase from the fungus *Curvularia inaequalis* (Van Schijndel, et al., *Eur. J. Biochem.*, 225:151–157 (1994)). A vanadate requirement for algal haloperoxidase was first described by Vilter (Vilter, H., *Biological Systems*, 31, *Vanadium and its role in life*, Sigel, et al. (Eds.), Marcel Dekker, New York, N.Y., pp. 325–362 (1995)).

The specific bromoperoxidase activity of the native Fucus enzyme is several fold higher (Butler, et al.) than the other algal enzymes for which at least partial sequences have been reported, *Ascophyllim* (Vilter 1995) and *Corallina* (Shimonishi, et al. FEBS Letters, 428, 105–110 (1998)), and higher specific activity than the *Curvularia* fungal chloroperoxidase (van Schijndel et al. BBA 1161:249–256 (1993)).

Extracted and partially purified bromoperoxidase from the red alga *Corallina officinalis* is commercially available from Sigma Chemical Company. Sigma has also investigated immobilization of enzyme on agarose beads (Sheffield, et al., *Phytochemistry*, 38:1103–1107 (1995)) and on cellulose acetate membrane (Sheffield, et al., *Biotechnology Techniques*, 8:579–582 (1994)) for repetitive catalysis of bromination reactions in flow-through reactors in enzyme-driven preparative organic chemistry. Many industrial uses for stable soybean peroxidase are envisioned by A. Pokora of Enzymol International, Inc. as described by Wick (Wick, C. B., *Genetic Engineering News*, 16(3): 1, 18–19). Recombinant enzyme biotechnology is of current industrial interest because enzymes are safe, low-polluting alternatives to chemicals in many applications, and can be modified by protein engineering to fit the requirements of specific applications (Kelly, E. B. *Genetic Engineering News*, 16(5):1, 30, 32 (1996) Lovqvist, et al., *Nuclear Medicine and Biology*, 22:125–131 (1995)). Peroxidases can also be incorporated into moldable plastics (Service, R. F., *Science* 272:196–197 (1996)).

Multiple representatives of other classes of peroxidases have been produced in recombinant form. A heme peroxidase, manganese peroxidase from the fungus *Phanerochaete chrysosporidium*, was expressed in recombinant form and refolded for activity (Whitwam, R. E., *Biochem. Biophys. Research. Communications*, 216:1013–1017 (1995)). Recombinant horseradish peroxidase isozyme C (a heme peroxidase) for use in chemiluminescent labeling in molecular biology and biotechnology applications has been described (EP 0299682, WO 89/03424). Recombinant non-heme haloperoxidases have been prepared from the bacteria, *Pseudomonas pyrrocinia* (Wolfframm, et al., *Gene* 130:131–135 (1993)) and two related *Streptomyces aureofaciens* enzymes (van Pée, K. H., *J. Bacteriol.*, 170:5890–5894 (1988); Pfeifer, et al., *J. Gen. Microbiol.* 138:1123–1131 (1992)).

Despite the interest in vanadium haloperoxidases, there are relatively few reports in the literature of the cloning and recombinant expression of a vanadium haloperoxidases. Shimonshi et al. *FEBS Lett*. 428:105–110 (1998) described cloning of the enzyme from *Corallina pilulifera*. Cloning of the *Curvularia* gene is described by Henrika, et al. *PNAS* 94,2145–2149 (1997) and 95/27046. A partial sequence of the *Ascophyllum* gene is described in Vitel (1995). There is a need in the art for efficient means for producing vanadium haloperoxidases using techniques such as recombinant expression. The present invention addresses these and other needs.

SUMMARY OF THE INVENTION

The present invention provides isolated nucleic acids comprising a polynucleotide sequence encoding a vanadium bromoperoxidase polypeptide comprising an amino acid sequence having at least 90% amino acid sequence identity to an amino acid sequence from residue 441 to residue 676 as set forth in SEQ ID NO:2. The polypeptides of the invention catalyze the oxidation of o-dianisidine (ODA) when complexed with a vanadium ion. The polynucleotide sequence usually has at least 60% sequence identity to a sequence as set forth in SEQ ID NO:1.

The polypeptides of the invention can be of various sizes. Typically, the polypeptides have molecular weight of about 73.4 kD, usually the polypeptide has a molecular weight of about 58 kD, or sometimes at least about 40 kD.

The invention also provides expression cassettes comprising a heterologous promoter operably linked to the polynucleotide sequences of the invention. The promoter can be active in a prokaryotic cell, such as a bacterium. Also provided are cells the expression cassette of the invention.

The invention further provides methods for enzymatically halogenating or oxidizing a compound using the polypeptides of the invention.

Definitions

A "vanadium bromoperoxidase polypeptide" of the invention is an isolated protein capable of catalyzing the oxidation of o-dianisidine (ODA) when complexed with a vanadium ion. Vanadium bromoperoxidases of the invention can also be identified by the presence of a conserved C terminal region located from residue 441 to residue 676 in SEQ ID NO:2. Polypeptides of the invention typically have a sequence at least about 90% identical (as determined below), usually at least about 95% identical to the sequence from residue 441 to residue 676 in SEQ ID NO:2. One of skill will recognize that the sequence of the polypeptide can be altered without substantially altering activity of the polypeptide (e.g., by conservative substitutions). In addition, as explained below, less conservative modifications (e.g., substitutions, additions, and deletions) can be made to facilitate proper refolding, purification, and the like, as desired.

Full length vanadium bromoperoxidase polypeptides of the invention typically have a mass of about 73.4 kD, and have a sequence as shown in SEQ ID NO:2. One of skill will recognize that shorter vanadium bromoperoxidase polypeptides can also be used. For instance, the polypeptides can consist essentially of the C terminal region described above. The polypeptides may thus comprise from about 300 amino acids to about 680 amino acids, or from about 500 to about 600 amino acids. Exemplary polypeptide having a mass of about 60 kD and 40 kD are described in detail below.

A "polynucleotide sequence encoding a vanadium bromoperoxidase polypeptide" of the invention is a polynucleotide which encodes a vanadium peroxidase polypeptide as described above. An exemplary sequence is provided in SEQ ID NO:1. One of skill can readily make nucleic acid molecules encoding polypeptides within the scope of the invention. Thus, the nucleic acids of the invention can be altered by substitutions, deletions, and additions, as desired. Polynucleotide sequences of the invention will typically be at least about 60%, usually at least about 70%, more usually at least about 80%, and often at least about 90% or 95% identical to SEQ ID NO:1. Polynucleotides of the invention can also be identified by their ability to hybridize under defined conditions to a nucleic acid having SEQ ID NO:1. Means for determining this are described in detail below.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual organism or cell is a polynucleotide which is introduced into the organism or cell using genetic engineering techniques.

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

In the case where the inserted polynucleotide sequence is transcribed and translated to produce a functional polypeptide, one of skill will recognize that because of codon degeneracy a number of polynucleotide sequences will encode the same polypeptide. In addition, the term specifically includes those sequences substantially identical (determined as described below) with polynucleotide sequences disclosed here.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4: 11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90, 95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of an algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altshul, et al., *J. Mol. Biol.*, 215:403–410 (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising nucleic acids useful in the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2× SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

DETAILED DESCRIPTION OF THE INVENTION

Figure 1:
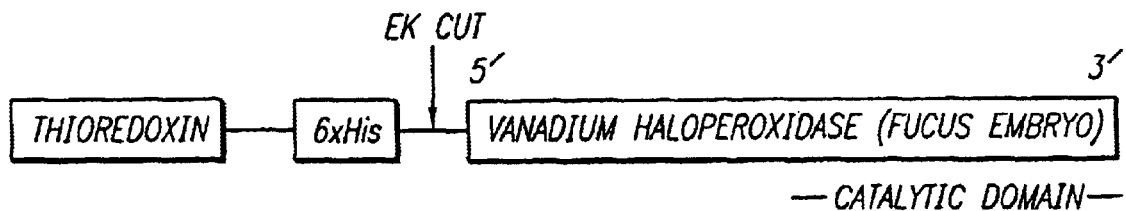
FIG. 1 is a schematic diagram of recombinant constructs of the invention.

The practice of this invention involves the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well-known to persons of skill. Examples of these techniques and instructions sufficient to direct persons of skill through many cloning exercises are found in Sambrook et al., *Molecular Cloning: A Laboratory Manual*, 2nd Ed., Vols. 1–3, Cold Spring Harbor Laboratory (1989); Berger and Kimmnel, *Guide to Molecular Cloning Techniques, Methods in Enzymology* volume 152 Academic Press, Inc., San Diego, Calif.; and *Current Protocols in Molecular Biology*, F. M. Ausubel et al., eds., Current Protocols, a joint venture between Greene Publishing Associates, Inc. and John Wiley & Sons, Inc. (1994 Supplement).

Preparation of Nucleic Acids of the Invention

Nucleic acids encoding vanadium bromoperoxidase polypeptides of this invention can be prepared by any suitable method known in the art, including, for example, cloning and restriction of appropriate sequences or direct chemical synthesis by methods such as the phosphotriester method of Narang et al. (1979) *Meth. Enymol.* 68: 90–99; the phosphodiester method of Brown et al. (1979) *Meth. Enymol.* 68: 109–151; the diethylphosphoramidite method of Beaucage et al. (1981) *Tetra. Lett.*, 22: 1859–1862; and the solid support method of U.S. Pat. No. 4,458,066.

In one preferred embodiment, the desired nucleic acids encoding a vanadium bromoperoxidase are isolated by routine cloning methods. A nucleotide sequence encoding the enzyme (as provided below, for example) is used to construct probes that specifically hybridize to a bromoperoxidase gene in a genomic DNA sample, or to mRNA in a total RNA sample (e.g., in a Southern or Northern blot). Once the target nucleic acid is identified, it can be isolated according to standard methods known to those of skill in the art.

The desired nucleic acids can also be cloned using well known amplification techniques. Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; Van Brunt (1990) *Biotechnology* 8: 291–294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039. Suitable primers for use in the amplification of the nucleic acids of the invention are described in the Example Section, below.

The desired nucleic acid can also be cloned by detecting its expressed product by means of assays based on the physical, chemical, or immunological properties of the expressed protein. For example, one can identify a cloned bromoperoxidase nucleic acid by the ability of a polypeptide encoded by the nucleic acid to catalyze the oxidation of o-dianisidine HCl (ODA) as described in the examples below.

In some embodiments, it may be desirable to modify the bromoperoxidase nucleic acids of the invention. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81–97, Roberts et al. (1987) *Nature* 328: 731–734. The modified polypeptides can be tested for activity using the ODA assays described below.

Preparation of Expression Cassettes Encoding Bromoperoxidase Polypeptides of the Invention The nucleic acid sequences of the invention are incorporated into expression cassettes for high level expression in a desired host cell according to techniques well known to those of skill in the art. The particular host cell used is not critical to the invention and can be either a prokaryotic or eukaryotic cell, as described below.

A typical expression cassette contains a promoter operably linked to the desired DNA sequence. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21–25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

Either constitutive or regulated promoters can be used in the present invention. Regulated promoters can be advantageous because the host cells can be grown to high densities before expression of the bromoperoxidase polypeptides is induced. High level expression of heterologous proteins slows cell growth in some situations. Regulated promoters especially suitable for use in *E. coli* include the bacteriophage lambda $P_L$ promoter, the hybrid trp-lac promoter (Amann et al., *Gene* (1983) 25: 167; de Boer et al., *Proc. Natl. Acad. Sci. USA* (1983) 80: 21, and the bacteriophage T7 promoter (Studier et al., *J. Mol. Biol.* (1986); Tabor et al., (1985). These promoters and their use are discussed in Sambrook et al., supra.

For expression of the polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in Bacillus in addition to *E. coli*.

A ribosome binding site (RBS) is conveniently included in the expression cassettes of the invention. An RBS in *E. coli*, for example, consists of a nucleotide sequence 3–9 nucleotides in length located 3–11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, N.Y.).

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297–16302.

The polypeptides can be expressed intracellularly, or can be secreted from the cell. Intracellular expression often results in high yields. If necessary, the amount of soluble, active polypeptide may be increased by performing refolding procedures (see, e.g., Sambrook et al., supra.; Marston et al., *Bio/Technology* (1984) 2: 800; Schoner et al., *Bio/Technology* (1985) 3: 151).

In embodiments in which the bromoperoxidase polypeptides are secreted from the cell, either into the periplasm or into the extracellular medium, the DNA sequence is linked to a cleavable signal peptide sequence. The signal sequence directs translocation of the bromoperoxidase polypeptide through the cell membrane. An example of a suitable vector for use in *E. coli* that contains a promoter-signal sequence unit is pTA 1529, which has the *E. coli* phoA promoter and signal sequence (see, e.g., Sambrook et al., supra.; Oka et al., *Proc. Natl. Acad. Sci. USA* 82: 7212 (1985); Talmadge et al., *Proc. Natl. Acad. Sci. USA*, 77:3988 (1980); Takahara et al., *J. Biol. Chem.*, 260:2670 (1985)).

One of skill would recognize that other modifications can be made to the bromoperoxidase polypeptides without diminishing their biological activity. Some modifications may be made to facilitate the cloning, expression, and the like. Such modifications are well known to those of skill in the art and include, for example, a methionine added at the amino terminus to provide an initiation site, or additional amino acids that form an epitope tag (e.g., poly His) placed on either terminus to facilitate purification. In addition, one of skill will recognize that fusion proteins with various heterologous protein sequences can be prepared. For example, overexpression of a protein can lead to the accumulation of folding intermediates which have a tendency to aggregate. Production of fusion proteins including sequences, such as bacterial thioredoxin, can be used to facilitate proper folding. The polypeptides of the invention can also be linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.).

For certain applications, it may be desirable to cleave the non-bromoperoxidase amino acids from the fusion protein after purification. This can be accomplished by any of several methods known in the art, including cleavage by cyanogen bromide, a protease (e.g., enterokinase), or by Factor $X_a$, (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

A suitable system for obtaining recombinant proteins from *E. coli* which maintains the integrity of their N-termini has been described by Miller et al. *Biotechnology* 7:698–704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

Expression of Bromoperoxidase Polypeptides of the Invention

Bromoperoxidases of the invention can be expressed in a variety of host cells, including *E. coli*, other bacterial hosts, yeast, and various higher eukaryotic cells such as algal cells. For example microalgal expression systems, useful in the invention include the diatom *Phaeodactylum tricornutum* (Apt et al. *J. Phycol.* 32:4 (1996)).

Examples of useful bacteria include, but are not limited to, *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus*. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The expression vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant bromoperoxidase polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification*., Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

The purified bromoperoxidase polypeptides of the invention can be used in a number of industrial applications. The polypeptides can be used for any purpose to which prior art haloperoxidases are used. For instance, the polypeptides can be used to halogenate various substrates, including proteins. For instance the polypeptides can be used to produce epoxides from alkenes, halogenated ketones from alkynes, to produce alpha, gamma-halohydrins from cyclopropanes, and to produce dihalogenated products from alkenes and alkynes. In addition, the ability of the polypeptides to oxidize various compounds make them useful, for instance, in signal generating systems in place of horseradish peroxidase. Thus, the bromoperoxidase polypeptides of the invention can be used as a component in assays as described in WO 97/09619. The polypeptides can also be as enzymatic antimicrobial agents (see, e.g., WO 95/27046). Other uses include production of phenolic adhesives as described in U.S. Pat. No. 5,520,727.

EXAMPLE 1

This example describes the cloning of a vanadium bromoperoxidase gene of the invention.

Materials and Methods

DNA Library. A *Fucus distichus* 2-cell embryos c-DNA library was prepared the λ-ZipLoxL1 plasmid (Gibco BRL, Gaithersburg, Md.) and is described in Goodner, et al., *Plant Physiology*, 107:1007–1008 (1995).

Antibody Screening. An antibody to *Corallina vancouverensis* vanadium peroxidase was prepared which identified *Fucus distichus* vanadium peroxidase on Western blots of crude extracts.

DNA Hybridization Method. Hybridization probes were prepared at the second and near the third regions shown to be conserved between *Curvularia* and *Ascophyllum* vanadium peroxidase active sites by Messerschmidt, et al., *PNAS*, 93:392–396 (1996). Hybridization probes of 51 base pairs were designed with Oligo 5.0 Primer Analysis Software (National Biochemicals, Plymouth, Minn.), synthesized by Anagen (Palo Alto), and digoxigenin-labeled at the 5' end with the Genius system (BMB Biochemicals, Durham, N.C.). The sequence of the probe for the second conserved site was:
CCAACGCACCCTTCGTACCCGTCTGGCCACGCTAC CCAAAACGGAGCATTT (SEQ ID NO:3).

The sequence of the probe for the third conserved site was:
CCGTACGAACACTTCACCAGGAGCTGATGACTTTC GCCGAGGAATCCACCT (SEQ ID NO:4).

Sequencing

Sequencing of the *Fucus* vanadium peroxidase clone was accomplished by primer walking. M13 universal primers and primers designed from Fucus and Ascophyllum Vanadium haloperoxidase sequences with Oligo software and synthesized by Operon (Alameda, Calif.). ABI dye-terminator sequencing was done by the UCB Molecular and Cellular Biology DNA Sequencing Facility in Barker Hall.

Homology

DNA and protein searches on databases accessible online through GenBank using the BLAST algorithm (Altshul, et al., *J. Mol. Biol.*, 215:403–410 (1990)).

Protein Expression

In order to optimize correct folding for peroxidase activity, recombinant *Fucus* vanadium peroxidase constructs were prepared and expressed in *E. coli* as fusion proteins with thioredoxin at the N-terminal end (pET-32 LIC Ligation Independent Cloning vector, Novagen, Madison, Wis.). This vector produces a high level of expression of soluble recombinant proteins in *E. coli* cytoplasm. The expressed protein is fused with an N-terminal thioredoxin (Trx.Tag™), S.Tag™ and His.Tag™, for optimizing correct protein folding, detection and purification, respectively (Novagen). In addition, an enterokinase (EK) cleavage site is located at the N-terminal end of the inserted protein so that native protein can be cleaved from the 19 kDa tagged peptide following expression. Three sizes of constructs were prepared for confirmation of the active site domain at the 3' end, as suggested by the minimal fungal-Ascophyllum homology reported at the active site (Messerschmidt, et al., *PNAS*, 93:392–396 (1996)). Expression constructs were prepared for the full length *Fucus* bromoperoxidase and two 5'-truncated forms, rVPx1, rVPx2, and rVPx3, corresponding to 100%, 80% and 54% of the full length sequence, respectively. The cloned λ-ZipLox plasmid containing the *Fucus* vanadium bromoperoxidase cDNA was used as the template for PCR amplification with Vent DNA polymerase (New England Biolabs, Beverly, Mass.).

The following *Fucus* peroxidase LIC primers were designed with Oligo software (National Biosciences, Inc., Plymouth, Minn.) and pET-32 LIC sequences necessary for incorporation into the vector. Primers for the 5' end were: GACGACGACAAGATGCTTTGCCATGCAGCGGACA (SEQ ID NO:5) (34 bp) for the full length construct, GACGACGACAAGATGGCGCCGAATAGAAGGGA CAA (SEQ ID NO:6) (35 bp) for the mid length construct, and GACGACGACAAGATGCTCTTCCGAGCGACCTTC (SEQ ID NO:7) (33 bp) for the short construct. One 3'-primer, GAGGAGAAGCCCGGTTGCACTAAGC-CTGGCAGT (SEQ ID NO:8) (33 bp) was used for all three constructs. PCR was carried out for 30 cycles of 3 min at 94°, 1.5 min at 55° C. and 2.3 min at 72° C., in 7 mM MgSO4 for the full length construct and 4 mM MgSO4 for the two truncated constructs. The PCR products were electrophoresed in 1.5% agarose and stained with ethidium bromide. DNA was extracted from the excised bands in GenElute minus EtBr spincolumns (Supelco, Bellefonte, Pa.) and precipitated with ethanol.

Ligation independent cloning was carried out according to the pET-32 LIC protocol (Novagen), with a T4 DNA ligase (GibcoBRL, Grand Island, N.Y.) step added prior to transformation for the full length construct. The recombinant plasmids were transformed into the NovaBlue strain of *E. coli* according to the Novagen protocol. In all bacterial strains transformed, plasmid clones containing peroxidase inserts were identified by PCR of partial Fucus peroxidase sequences with Taq polymerase (Promega, Madison, Wis.) in 1.6–3.75 mM MgCl2 for 30 cycles of 3 min at 94°, 1.5 min at 45° and 2 min at 72°, followed by agarose electrophoresis. Plasmids cloned from NovaBlue cells were expressed in BL21(DE3), BL21(DE3) pLysS and AD494 (DE3) *E. coli* cells (Novagen). The AD494strain is deficient in thioredoxin reductase, which results in an appropriate redox potential for correct folding of eukaryotic proteins (Novagen). Induced bacterial cytoplasmic protein preparations were examined by protein electrophoresis, and the products were tested for vanadium-dependent peroxidase activity. Proteins were expressed for 0, 0.5, 1.5 and 3 h after induction of protein synthesis with IPTG (isopropylthio-b-galactoside). Bacterial lysates were prepared immediately after protein expression.

The recombinant bromoperoxidase proteins were immediately purified from bacterial cytoplasmic proteins by affinity chromatography. The HisTag (a sequence of 6 histidines, 6×His) in the fusion protein was bound to a nickel nitrilo-acetic acid (Ni+2-NTA) agarose column (Sigma, St. Louis, Mo.) according to the standard Qiagen protocol. The bound recombinant protein containing 6×His was eluted with 1M imidizole in 20 mM Tris-HCl pH 7.9 and 500 mM NaCl. Denatured protein samples were electrophoresed in 8% polyacrylamide gels containing 4% SDS, fixed and stained with Coomassie Brilliant Blue R250. The recombinant vanadium peroxidases (rVPx) were tested for vanadium-dependent peroxidase activity on dot blots. A preliminary in vitro expression experiment was carried out for the three LIC constructs in a bacteriophage transcription system linked with a rabbit reticulocyte translation system (Single Tube Protein System 2, T7, Novagen), and the products were tested for vanadium-dependent peroxidase activity on dot blots.

Vanadium Peroxidase Activity Assay

Peroxidase activity with ODA (o-dianisidine HCl, Sigma) as the substrate was detected by dot blotting 1 μL of enzyme solution onto positively charged nylon membranes (Biodyne B, Pall Corp., Port Washington, N.Y.). Substrate solution contained 100 mM Tris-HCl, pH 8.0, 10 mM KBr, 0.25 mM urea-H2O2, and 1 mM ODA (Sigma). Quantitites of dry KBr, urea-$H_2O_2$ and ODA were estimated for daily substrate solutions.

RVPx were rapidly revanadated with trace levels of vanadium. 1 μL of 100 mM sodium orthovanadate in a 2 μL pipettor tip was ejected from the tip. The "vanadated" empty tip was then inserted into a 5–10 μL drop of enzyme solution on a piece of Parafilm (Fisher, Hayward, Calif.) and pipetted in and out 5 times. After waiting 1–5 min, 1 AL of the revanadated rVPx was pipetted onto the nylon membrane and air dried for a few minutes. While strong peroxidase activity was visible in a few minutes, the membrane was incubated in the ODA solution overnight.

Antibody Labeling on Membranes (Plaque Lifts, Dot Blots and Western Blots)

The membranes were blocked overnight at 4° C. in 100 mM Tris-HCl pH 8.0+4% skim milk+0.1% tween -20 and then incubated for 3 h at 37° C. in mouse ascites antibody to *Corallina* vanadium peroxidase or mouse ascites control antibody (Sigma) diluted 1:1,000 in blocking solution. The blots were washed 3× in blocking solution and incubated in alkaline phosphatase-conjugated anti-mouse second antibody (diluted 1:5,000) for 1 h at room temperature. They were then washed 3× in blocking solution and rinsed in alkaline buffer (100 mM NaCl+100 mM Tris-HCl at pH 9.5.+50 mM MgCl2). Chemiluminescence was detected by of CPD-Star (BMB, Durham, NC) (diluted 1: in alkaline buffer) and exposed to X-ray film (Kodak) for 2 h. Alternative colorigenic detection was by overnight incubation in NBT/BCIP substrate (Pierce, Rockford, Ill.).

Results

*Fucus* cDNA Library Screening

The fusion protein for the VPx clone which was expressed during cDNA screening was apparently truncated prior to the VPx start codon, at a TGA stop codon located at bases 82–84 in the 5' UTR. This truncation upstream of the VPx coding sequence caused a lack of VPx protein expression during screening, explaining the lack of a-VPx antibody labeling during extensive screening. Therefore, two 51 bp DNA probes based on two small regions of homology at the active site between *Curvularia* chloroperoxidase and *Ascophyllum* bromoperoxidase (Messerschmidt, et al., *PNAS*, 93:392–396 (1996)) were used to screen the Fucus embryo cDNA library. Only one clone was identified which was labeled with both of the VPx DNA probes after extensive screening. This clone was about 3 kb in size after Not I/Sal I excision from the plasmid.

Fucus Vanadium Peroxidase Sequence

The sequence of the VPX from 2-cell *Fucus gardneri* embryos is shown in SEQ ID NO:1. The 2931 base pairs in the *Fucus* cDNA clone includes 227 bases in the 5' UTR, 2031 bases in the coding region and 673 bases in the 3' UTR. The 5' UTR is a partial sequence, and the 3' UTR is complete. Translation of the VPx coding sequence produces a 73,353 Da protein containing 676 amino acids. No obvious leader peptide sequence was detected although VPx is secreted (Vreeland, et al., *Molecular Biology of the Cell* 7 (Supplement), 304a (1996)).

A 73.4 kDa *Fucus* monomer would be the largest known VPx monomer, although the molecular mass of the native *Fucus* enzyme is unknown. The 73.4 kDa size is larger than the 60 kDa VPx monomer from a related brown alga, *Ascophyllum nodosum*, as well as larger than the 67.5 kDa fungal *Curvularia inaequalis* chloroperoxidase monomer (Simons, et al., *European Journal of Biochemistry*, 229:566–574 (1995)). The *Fucus* VPx monomer comigrated with the monomer of the red alga *Corallina vancouverensis* on PAGE gels (Vreeland, et al., *Molecular Biology of the Cell* 7 (Supplement), 304a (1996)). The *C. officinalis* and *C. pilulifera* VPx monomers are approximately 64 kDa based on SDS PAGE data (Itoh, et al., *J. Biological Chemistry* 261:5194–5200 (1986); Sheffield, et al., *Phytochemistry*, 32:21–26 (1993); Rush, et al., *FEBS Letters*, 359:244–246 (1995)), and the *Fucus* VPx monomer might therefore be expected to be a similar size. However, the related *Fucus* and *Ascophyllum* brown algal VPx monomer sizes differ, and it is also possible that the *C. vancouverensis* monomer size may differ from the published *C. officinalis* and *C. pilulifera* monomer size.

Alternative explanations include utilization of the third start codon in the *Fucus* VPx sequence to produce a 64,471 Da protein of 596 amino acids. Utilization of the third start codon is supported by the lack of a TATA box upstream of the first two start codons, and the presence of a TATA box 79 bp upstream of the third in-frame ATG. Also possible are different protein shape and/or charge properties resulting in electrophoretic comigration of *Fucus* and *C. vancouverensis* monomers.

The *Fucus* and *C. vancouverensis* multimers also comigrated, implying that the *Fucus* multimer may be a dodecamer (Vreeland, et al., *Molecular Biology of the Cell* 7 (Supplement), 304a (1996)) although the *Ascophyllum* multimer is a dimer (Vilter 1995), since the *C. officinalis* and *C. pilulifera* multimers appear to be dodecamers (Sheffield, et al., *Phytochemistry*, 32:21–26 (1993); Rush, et al. *FEBS Letters*, 359:244–246 (1995); Itoh, et al., *J. Biological Chemistry* 261:5194–5200 (1986)). Although the C-terminal catalytic domain appears to be similar in *Fucus* and *Ascophyllum* VPx, their self-associating domains are likely to differ due to their different monomer sizes. The *Fucus* VPx may contain more than one self-associating domain if it contains the double hexameric ring arrangement as found for the *C. pilulifera* VPx by Itoh, et al., *J. Biological Chemistry* 261:5194–5200 (1986), and this may partially account for the larger size of the *Fucus* VPx in the N-terminal region.

The *Fucus* and *Ascophyllum* brown algal VPx were 87.2% identical for 709 base pairs of DNA and 85.8% identical for 232 amino acids for the published partial C-terminal VPx sequence of *Ascophyllum* (Vilter 1995) when calculated from the best match of the *Fucus* data with the published *Ascophyllum* peptide and translated sequences.

The *Fucus* sequence contains three conserved vanadium-binding regions (Messerschmidt et al.). The three conserved vanadium-binding regions are as follows: (1) amino acids 452–473-AQRASCYQKWQVHRFARPEALG (SEQ ID NO:9); (2) amino acids 528–546-PTHPSYPSGHATQNG AFAT (SEQ ID NO:10) and (3) amino acids 591–609 NKLAVNVAFGRQMLGIHYRFD (SEQ ID NO:11). -In the three conserved vanadium-binding regions the *Fucus* and *Ascophyllum* amino acid sequences differ only at two locations in the first conserved region (alanine at F455 substituted for serine at *Ascophyllum* 19, and cysteine at *Fucus* 457 substituted for tryptophan at *Ascophyllum* 21). These two amino acid differences are therefore likely to be related to the greater specific activity of the *Fucus* enzyme, as are other amino acid sequence differences in the catalytic domain (amino acids *Fucus* 441–676). A major difference between the *Fucus*, *Ascophyllum* and *Corallina* algal bromoperoxidases and the fungal chloroperoxidases and various phosphatases is the additional basic amino acids in the first conserved domain of the bromoperoxidases, histidine at *Fucus* 464 and leucine at *Fucus* 472 for the brown algal enzymes, with threonine instead of leucine for the *Corallina* enzyme. These additional amino acids in the first conserved region are likely to be related to the greater activity of the bromoperoxidases with bromide, which is larger than the chloride ion.

Bacterial Expression of *Fucus* Vanadium Peroxidase Constructs.

The three recombinant *Fucus* VPx proteins (rVPx1, rVPx2, rVPx3, FIG. 1) were expressed as soluble cytoplasmic proteins in both BL21 (DES) and AD494 strains of *E. coli* at the expected sizes of recombinant proteins. All of the recombinant proteins were seen as major bands against the background of bacterial proteins. This represents production of about 1–10 mg/100 mL of recombinant proteins, as estimated from the intensity of Coomassie blue-stained bands.

After Ni—NTA column purification, peroxidase activity for rVPx expressed by AD494 cells was tested on dot blots with 0-dianisidine as substrate. No peroxidase activity was detected in the absence of added vanadium, although *E. coli* contains an 80 kDa 0-dianisidine-reactive peroxidase. This result with an extremely sensitive activity assay also demonstrates that the single affinity purification step removed significant contamination by bacterial proteins.

Peroxidase activity was detected in all three rVPx constructs immediately following protein expression and purification, but only in the presence of added vanadium. The activity was relatively weak, and decreased with smaller rVPx construct size. However, after overnight treatment at −20° C., activity was much stronger and of similar intensity for all three construct sizes. Like native algal VPx, the recombinant forms bound to positively charged nylon membranes but did not bind to nitrocellulose membranes. However, the recombinant forms did not bind as tightly to nylon membranes.

The three sizes of rVPx were also expressed in an in vitro rabbit reticulocyte system. It was clear that expression of all three sizes of rVPx occurred, although background peroxidase activity was seen in this eukaryotic system.

Discussion

ODA is a common substrate for heme peroxidases such as horseradish peroxidase and other peroxidases. The product of ODA oxidation by algal vanadium peroxidase was not halogenated, although it is not known whether ODA oxidation by rVPx involves a halogenated intermediate or singlet O2 production. The expression of active rVPx in E. coli demonstrates that glycosylation is not necessary for enzyme activity, and, indeed, the native enzyme is probably not glycosylated. Activity of recombinant enzyme shows that it can be folded correctly in bacterial cytoplasm, as well.

The above examples are provided to illustrate the invention but not to limit its scope. Other variants of the invention will be readily apparent to one of ordinary skill in the art and are encompassed by the appended claims. All publications, GenBank Accession references (sequences), patents and patent applications cited herein are hereby expressly incorporated by reference for all purposes.

What is claimed is:

1. An isolated polypeptide comprising an amino acid sequence, which consists of a sequence from residue 441 to residue 676 as set forth in SEQ ID NO:2, wherein the polypeptide catalyzes oxidation of o-dianisidine (ODA) when complexed with a vanadium ion, has at least 80% amino acid sequence identity to a polypeptide as set forth in SEQ ID NO:2, and has a molecular weight of between about 40 to about 60 kDa.

2. The isolated polypeptide of claim 1, wherein the polypeptide has a molecular weight of about 58 kD.

3. The isolated polypeptide of claim 1, wherein the polypeptide has a molecular weight of about 40 kD.

4. The isolated polypeptide of claim 1, wherein the polypeptide is immobilized on a solid surface.

5. The isolated polypeptide of claim 1, wherein the polypeptide further comprises a cleavable linker sequence.

6. The isolated polypeptide of claim 5, wherein the cleavable linker sequence is an enterokinase cleavable linker sequence.

7. The isolated polypeptide of claim 1, wherein the polypeptide further comprises an epitope tag.

8. The isolated polypeptide of claim 7, wherein the epitope tag comprises a plurality of histidine residues.

9. The isolated polypeptide of claim 1, wherein the polypeptide further comprises a thioredoxin sequence.

10. A method for enzymatically halogenating a compound, the method comprising contacting the compound with an isolated polypeptide of claim 1.

11. The method of claim 10, wherein the compound is a protein.

12. A method for enzymatically oxidizing a compound, the method comprising contacting the compound with an isolated polypeptide of claim 1.

* * * * *

UNITED STATES PATENT AND TRADEMARK OFFICE
CERTIFICATE OF CORRECTION

PATENT NO. : 6,828,133 B2  Page 1 of 1
DATED : December 7, 2004
INVENTOR(S) : Valerie Vreeland et al.

It is certified that error appears in the above-identified patent and that said Letters Patent is hereby corrected as shown below:

Column 1,
Line 8, insert after the first paragraph under the title "RECOMBINANT VANADIUM HALOPEROXIDASES AND THEIR USES":
-- This invention was made with Government support under Grant No. 8905221, awarded by the National Science Foundation. The Government has certain rights in this invention. --

Signed and Sealed this

Thirty-first Day of May, 2005

JON W. DUDAS
*Director of the United States Patent and Trademark Office*